(12) United States Patent
McLean et al.

(10) Patent No.: US 8,394,108 B2
(45) Date of Patent: Mar. 12, 2013

(54) SCREW DRIVER FOR A MULTIAXIAL BONE SCREW

(75) Inventors: Scott McLean, Waterbury, CT (US); Steven Seyer, Shelton, CT (US)

(73) Assignee: Spine Wave, Inc., Shelton, CT (US)

( * ) Notice: Subject to any disclaimer, the term of this patent is extended or adjusted under 35 U.S.C. 154(b) by 0 days.

(21) Appl. No.: 13/118,868

(22) Filed: May 31, 2011

(65) Prior Publication Data

US 2011/0313471 A1    Dec. 22, 2011

Related U.S. Application Data

(63) Continuation-in-part of application No. 12/818,979, filed on Jun. 18, 2010.

(51) Int. Cl.
*A61B 17/88* (2006.01)
*A61B 17/86* (2006.01)

(52) U.S. Cl. ............... 606/104; 606/86 A; 606/306

(58) Field of Classification Search ............ 606/86 A, 606/246, 264–270, 300–301, 304–306, 104
See application file for complete search history.

(56) References Cited

U.S. PATENT DOCUMENTS

| | | |
|---|---|---|
| 2,248,054 A | 7/1941 | Becker |
| 4,238,339 A | 12/1980 | Khutoretsky et al. |
| 4,363,250 A | 12/1982 | Suga |
| 4,411,191 A | 10/1983 | Combeau |
| 4,411,259 A | 10/1983 | Drummond |
| 4,448,191 A | 5/1984 | Rodnyansky et al. |
| 4,657,001 A | 4/1987 | Fixel |
| 4,736,738 A | 4/1988 | Lipovsek et al. |
| 4,763,548 A | 8/1988 | Leibinger et al. |
| 4,913,134 A | 4/1990 | Luque |
| 5,049,151 A | 9/1991 | Durham et al. |
| 5,092,866 A | 3/1992 | Breard et al. |
| 5,139,499 A | 8/1992 | Small et al. |
| 5,242,443 A | 9/1993 | Kambin |
| 5,263,953 A | 11/1993 | Bagby |
| 5,354,292 A | 10/1994 | Braeuer et al. |
| 5,355,752 A | 10/1994 | Keenan et al. |
| 5,411,503 A | 5/1995 | Hollstien et al. |
| 5,423,819 A | 6/1995 | Small et al. |
| 5,439,464 A | 8/1995 | Shapiro |
| 5,458,608 A | 10/1995 | Wortrich |
| 5,649,931 A | 7/1997 | Bryant et al. |
| 5,667,513 A | 9/1997 | Torrie et al. |

(Continued)

FOREIGN PATENT DOCUMENTS

FR    2510022    1/1983

OTHER PUBLICATIONS

Synthes Spine, "Constellation CP System—Technique Guide", 2003, Synthes Spine, Inc., West Chester, PA 19380.

(Continued)

*Primary Examiner* — Kevin T Truong
*Assistant Examiner* — Larry E Waggle, Jr.
(74) *Attorney, Agent, or Firm* — Hoffmann & Baron, LLP (57) ABSTRACT

A screwdriver for driving a multi-axial its distal end for engaging the head of the bone screw for joint rotational movement. The screw driver includes an outer retention sleeve within which the inner shaft rotates freely. The outer retention sleeve releasably attaches to the yoke of the bone screw. In another configuration, the screwdriver comprises a screw engagement member affixed to the shaft for joint rotational movement therewith, the screw engagement member comprising a stop sized to seat within a slot of the bone screw yoke, the stop being configured to rotate the yoke upon rotation shaft. A releasable retention member is provided on the screw engagement member for releasably attaching the screwdriver to the bone screw.

7 Claims, 8 Drawing Sheets

U.S. PATENT DOCUMENTS

| | | | |
|---|---|---|---|
| 5,741,261 A | 4/1998 | Moskovitz et al. |
| 5,814,072 A | 9/1998 | Bonutti |
| 5,897,574 A | 4/1999 | Bonutti |
| 5,902,231 A | 5/1999 | Foley et al. |
| 5,910,141 A | 6/1999 | Morrison et al. |
| 5,948,002 A | 9/1999 | Bonutti |
| 5,954,635 A | 9/1999 | Foley et al. |
| 5,961,538 A | 10/1999 | Pedlick et al. |
| 5,961,554 A | 10/1999 | Janson et al. |
| 6,090,113 A | 7/2000 | Le Couedic et al. |
| 6,102,934 A | 8/2000 | Li |
| 6,183,472 B1 | 2/2001 | Lutz |
| 6,188,472 B1 | 2/2001 | Gage et al. |
| 6,189,422 B1 | 2/2001 | Stihl |
| 6,235,028 B1 | 5/2001 | Brumfield et al. |
| 6,440,133 B1 | 8/2002 | Beale et al. |
| 6,530,926 B1 | 3/2003 | Davison |
| 6,530,929 B1 | 3/2003 | Justis et al. |
| 6,660,006 B2 | 12/2003 | Markworth et al. |
| D488,229 S | 4/2004 | Rinner et al. |
| 6,716,218 B2 | 4/2004 | Holmes et al. |
| 6,793,656 B1 | 9/2004 | Mathews |
| 6,802,844 B2 | 10/2004 | Ferree |
| 6,830,574 B2 | 12/2004 | Heckele et al. |
| 6,945,933 B2 | 9/2005 | Branch et al. |
| 7,008,422 B2 | 3/2006 | Foley et al. |
| 7,011,660 B2 | 3/2006 | Sherman et al. |
| 7,160,300 B2 | 1/2007 | Jackson |
| 7,179,261 B2 | 2/2007 | Sicvol et al. |
| 7,188,626 B2 | 3/2007 | Foley et al. |
| 7,226,453 B2 | 6/2007 | Chao et al. |
| 7,250,052 B2* | 7/2007 | Landry et al. ............... 606/86 A |
| 7,306,603 B2 | 12/2007 | Boehm, Jr. et al. |
| 7,420,279 B2 | 9/2008 | Ohnishi et al. |
| 7,465,306 B2 | 12/2008 | Pond, Jr. et al. |
| 7,473,267 B2 | 1/2009 | Nguyen et al. |
| 7,476,240 B2 | 1/2009 | Raymond et al. |
| 7,491,208 B2 | 2/2009 | Pond, Jr. et al. |
| 7,491,218 B2 | 2/2009 | Landry et al. |
| 7,497,869 B2 | 3/2009 | Justis |
| 7,520,879 B2 | 4/2009 | Justis et al. |
| 7,527,638 B2 | 5/2009 | Anderson et al. |
| 7,563,264 B2 | 7/2009 | Landry et al. |
| 7,572,276 B2 | 8/2009 | Lim et al. |
| 7,588,575 B2 | 9/2009 | Colleran et al. |
| 7,588,588 B2 | 9/2009 | Spitler et al. |
| 7,597,694 B2 | 10/2009 | Lim et al. |
| 7,618,442 B2 | 11/2009 | Spitler et al. |
| 7,621,918 B2* | 11/2009 | Jackson ..................... 606/86 A |
| 7,648,506 B2 | 1/2010 | McCord et al. |
| 7,648,507 B2 | 1/2010 | Techiera et al. |
| 7,648,521 B2 | 1/2010 | Hestad |
| 7,666,188 B2 | 2/2010 | Anderson et al. |
| 7,666,189 B2 | 2/2010 | Gerber et al. |
| 7,686,814 B2 | 3/2010 | Lim et al. |
| 7,708,763 B2 | 5/2010 | Selover et al. |
| 7,758,584 B2 | 7/2010 | Bankoski et al. |
| 7,758,617 B2 | 7/2010 | Iott et al. |
| 8,231,635 B2 | 7/2012 | Sharifi-Mehr et al. |
| 2003/0208203 A1 | 11/2003 | Lim et al. |
| 2004/0138662 A1 | 7/2004 | Landry et al. |
| 2005/0065517 A1 | 3/2005 | Chin |
| 2005/0080418 A1 | 4/2005 | Simonsen et al. |
| 2005/0131422 A1 | 6/2005 | Anderson et al. |
| 2005/0154389 A1 | 7/2005 | Selover et al. |
| 2005/0228380 A1 | 10/2005 | Moore et al. |
| 2005/0245928 A1 | 11/2005 | Colleran et al. |
| 2005/0277934 A1 | 12/2005 | Vardiman |
| 2006/0025773 A1 | 2/2006 | Yevmenenko et al. |
| 2006/0084993 A1 | 4/2006 | Landry et al. |
| 2006/0111714 A1 | 5/2006 | Foley |
| 2006/0142761 A1 | 6/2006 | Landry et al. |
| 2006/0200135 A1 | 9/2006 | Sherman et al. |
| 2006/0229614 A1 | 10/2006 | Foley et al. |
| 2006/0247630 A1 | 11/2006 | Iott et al. |
| 2006/0264942 A1 | 11/2006 | Lim et al. |
| 2006/0264962 A1 | 11/2006 | Chin et al. |
| 2006/0276803 A1 | 12/2006 | Salerni |
| 2006/0293693 A1* | 12/2006 | Farr et al. ..................... 606/104 |
| 2007/0016188 A1 | 1/2007 | Boehm, Jr. et al. |
| 2007/0016198 A1 | 1/2007 | Boehm, Jr. et al. |
| 2007/0016199 A1 | 1/2007 | Boehm, Jr. et al. |
| 2007/0078460 A1 | 4/2007 | Frigg et al. |
| 2007/0167954 A1 | 7/2007 | Sievol et al. |
| 2007/0173745 A1 | 7/2007 | Diederich et al. |
| 2007/0185491 A1 | 8/2007 | Foley et al. |
| 2007/0198015 A1 | 8/2007 | Foley et al. |
| 2007/0233097 A1 | 10/2007 | Anderson et al. |
| 2008/0009864 A1 | 1/2008 | Forton et al. |
| 2008/0039838 A1 | 2/2008 | Landry et al. |
| 2008/0045970 A1* | 2/2008 | Saidha et al. ................. 606/104 |
| 2008/0051787 A1 | 2/2008 | Remington et al. |
| 2008/0077135 A1 | 3/2008 | Stad et al. |
| 2008/0077139 A1 | 3/2008 | Landry et al. |
| 2008/0119858 A1 | 5/2008 | Potash |
| 2008/0125788 A1 | 5/2008 | Cohen et al. |
| 2008/0200918 A1 | 8/2008 | Spitler et al. |
| 2008/0208258 A1 | 8/2008 | Foley et al. |
| 2008/0221583 A1* | 9/2008 | Sharifi-Mehr et al. ........ 606/104 |
| 2008/0243133 A1 | 10/2008 | Heinz |
| 2008/0312703 A1 | 12/2008 | Hestad et al. |
| 2009/0005814 A1 | 1/2009 | Miller et al. |
| 2009/0082666 A1 | 3/2009 | Geist et al. |
| 2009/0082811 A1 | 3/2009 | Stad et al. |
| 2009/0099172 A1 | 4/2009 | Cai et al. |
| 2009/0105774 A1 | 4/2009 | Jones et al. |
| 2009/0138056 A1 | 5/2009 | Anderson et al. |
| 2009/0143828 A1 | 6/2009 | Stad et al. |
| 2009/0182382 A1 | 7/2009 | Justis et al. |
| 2009/0264895 A1 | 10/2009 | Gasperut et al. |
| 2009/0264930 A1 | 10/2009 | McBride |
| 2009/0312797 A1 | 12/2009 | Lim et al. |
| 2010/0004695 A1 | 1/2010 | Stad et al. |
| 2010/0024487 A1 | 2/2010 | Khoo et al. |
| 2010/0030283 A1 | 2/2010 | King et al. |
| 2010/0036443 A1 | 2/2010 | Hutton et al. |
| 2010/0069972 A1 | 3/2010 | Jones et al. |
| 2010/0094359 A1 | 4/2010 | Techiera et al. |
| 2010/0137915 A1 | 6/2010 | Anderson et al. |
| 2010/0145348 A1 | 6/2010 | Marino |
| 2010/0145349 A1 | 6/2010 | Lim et al. |
| 2010/0145389 A1 | 6/2010 | Triplett et al. |
| 2010/0174326 A1 | 7/2010 | Selover et al. |
| 2010/0198272 A1 | 8/2010 | Keyer et al. |
| 2012/0203288 A1 | 8/2012 | Lange et al. |

OTHER PUBLICATIONS

Synthes Spine, "Cannulated Pangea System—Technique Guide", 2007, Synthes Spine, Inc., West Chester, PA 19380.

Peterson, M.D., Mark et al; "NuVasive Creative Spine Technology, SPHERX DBR Surgical Technique", 2005, NuVasive, Inc., San Diego, CA 92121.

Abbott, "PathFinder, Minimally Invasive Pedicle Screw System, Surgical Technique", Oct. 2008, 1199-0005-MKC Rev H per DCR 6005, Abbott Spine, Austin, Texas 78727.

Foley, M.D., Kevin T., Medtronic Sofamor Danek, "CD Horizon Sextant Rod Insertion System Surgical Technique, Minimal Access Spinal Technologies", 2002, Medtronic Sofamor Danek USA, Memphis, TN 38132.

Anderson, M.D., D. Greg et al.; "DePuySpine, Viper 2 Expedum System Guide", May 2008, MIO4-03-000, JC/UM, DePuySpine, Raynham, MA 02767.

Biomet Spine, Ballista™ Percutaneous Screw Placement System—Surgical Technique, 2008, Biomet, Inc., Parsippany, NJ 07054.

International Search Report and Written Opinion of the International Searching Authority issued in counterpart PCT Application No. PCT/US 12/37916, dated Aug. 8, 2012.

* cited by examiner

SCREW DRIVER FOR A MULTIAXIAL BONE SCREW

CROSS-REFERENCE TO RELATED APPLICATION

This is a continuation-in-part application of application Ser. No. 12/818,979 (the '979 Application), filed Jun. 18, 2010, now pending, which is herein incorporated by reference in its entirety.

BACKGROUND

The present disclosure contemplates instrumentation and procedures for achieving spinal fixation and more particularly to a screw driver for driving a bone screw into a vertebra of a patient.

Figure 1:
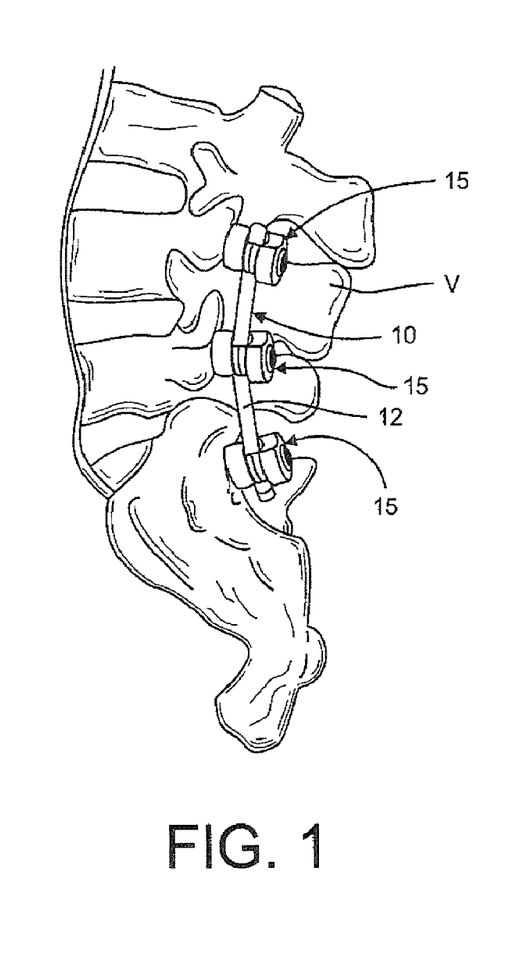
FIG. 1 is a representation of a portion of a patient's spine instrumented with a multi-level fixation system.

A typical spinal fixation system 10 as shown in FIG. 1 spans between successive vertebrae V of the spine. An elongated member, such as rod 12, extends along the length of the spine and provides an anchor point for connecting each vertebra to the rod. The rod is typically contoured to approximate the normal curvature of the spine for the particular instrumented spinal segments, which may include lordosis or kyphosis. Anchor devices 15 are provided for connecting the vertebral segments to the elongated member. These anchor devices may include hooks, bolts, screws or other means for engaging a vertebra. For the purposes of the present discussion, the anchor device 15 is a bone screw assembly, such as the screw assembly shown in FIG. 2.

Figure 2:
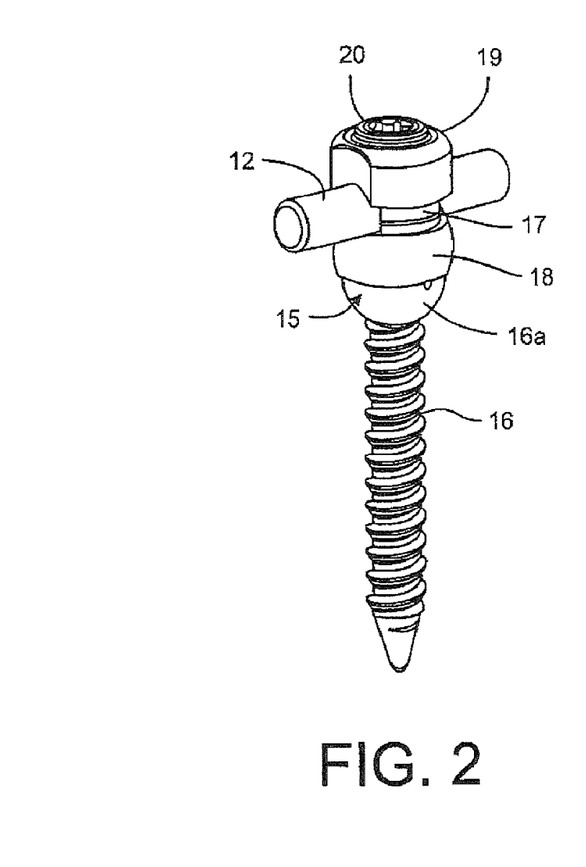
FIG. 2 is a perspective view of a bone engaging fastener in the form of a multi-axial pedicle screw suitable for use with a procedure disclosed herein.

The bone engaging fastener or screw assembly 15 includes a shank 16 that carries threads configured to engage vertebral bone. For instance, the fastener is a multi-axial pedicle screw with a shank that is threaded for engagement within the pedicle of the vertebra. The screw assembly further includes a head 16a by which the screw, and ultimately the vertebra, is fastened to the spinal rod 12. In particular, the head 16a supports a yoke 17 that is generally U-shaped to receive the spinal rod therethrough, as depicted in FIG. 2. The rod 12 may be supported in part by a collar 18 mounted over the head 16a of the bone screw. A cap 19 may carry a set screw 20 that locks the rod within the yoke 17 and thus fastens the rod 12 to the bone screw or the set screw 20 may be threadably attached directly to the yoke 17.

One embodiment of a bone screw assembly 15 is disclosed in co-pending, commonly assigned U.S. application Ser. No. 11/762,898 (the '898 Application), entitled "Multi-Axial Fixation Assembly", filed on Jun. 14, 2007 and published as No. 2008/0119858, the disclosure of which is incorporated herein by reference in its entirety. For the purposes of the present disclosure, the bone screw 15 may be constructed as disclosed in the '898 Application, although it is understood that other multi-axial bone screw configurations may be implanted using the instruments and procedures disclosed herein. In the multi-axial bone screw assembly 15 the yoke 17 is articulatingly attached to the threaded bone screw 16, and more specifically to the head 16a of the bone screw, so that the yoke 17 can adopt a range of spherical angles relative to the bone screw. Thus, the yoke can articulate relative to the bone screw fastened in the vertebra so that the slot 42 can be aligned to receive the connecting rod 12.

While in the past spinal fixation systems using screws of the '898 Application have been implanted in open procedures involving relatively large incisions through the patient's tissue with significant muscle retraction, more recent procedures have been developed to introduce spinal fixation systems in a minimally invasive or percutaneous manner. With multi-axial pedicle screws being primarily used in these systems there is a need to provide instruments for the surgeons to properly and readily insert such screws into the vertebrae of the spine for suitably receiving and supporting spinal connecting rods.

SUMMARY

The present invention is directed to a screwdriver for driving a multi-axial bone screw into a vertebra of the spine.

In accordance with one arrangement, a bone screw includes an elongate shaft having a threaded screw portion at the distal end and a screw head at the proximal end. A yoke is articulatingly attached to the screw head, the yoke having a slot therethrough for receiving a connecting rod and having an opening communicating with the screw head. The screwdriver comprises an elongate inner shaft having a distal end and a proximal end, the inner shaft defining a driving tip at the distal end configured to engage the screw head for rotation thereof. An outer retention sleeve disposed about the inner shaft has a distal end and a proximal end, the inner shaft being freely rotatable within the outer retention sleeve. The distal end of the outer retention sleeve is configured to releasably engage the yoke for joint rotational movement there with.

In accordance with another arrangement, the screwdriver comprises a screw engagement member affixed to the shaft for joint rotational movement therewith, the screw engagement member comprising a stop sized to seat within the slot of the bone screw yoke and configured to rotate the yoke upon rotation of the shaft. A releasable retention member is included on the screw engagement member for releasable attachment to the yoke. The releasable retention member may be releasably attached to an inner surface of the bone screw yoke or the outer surface.

DETAILED DESCRIPTION

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 3:
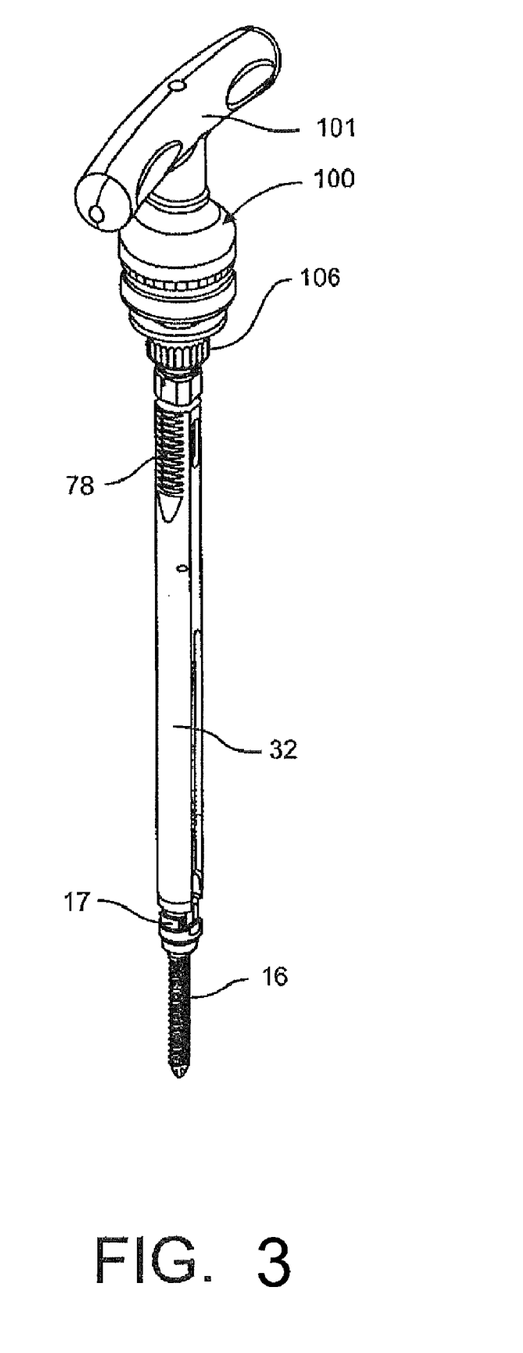
FIG. 3 is a perspective view of the bone screw and screw extension assembly with a screw driver mounted thereon.
Figure 4:
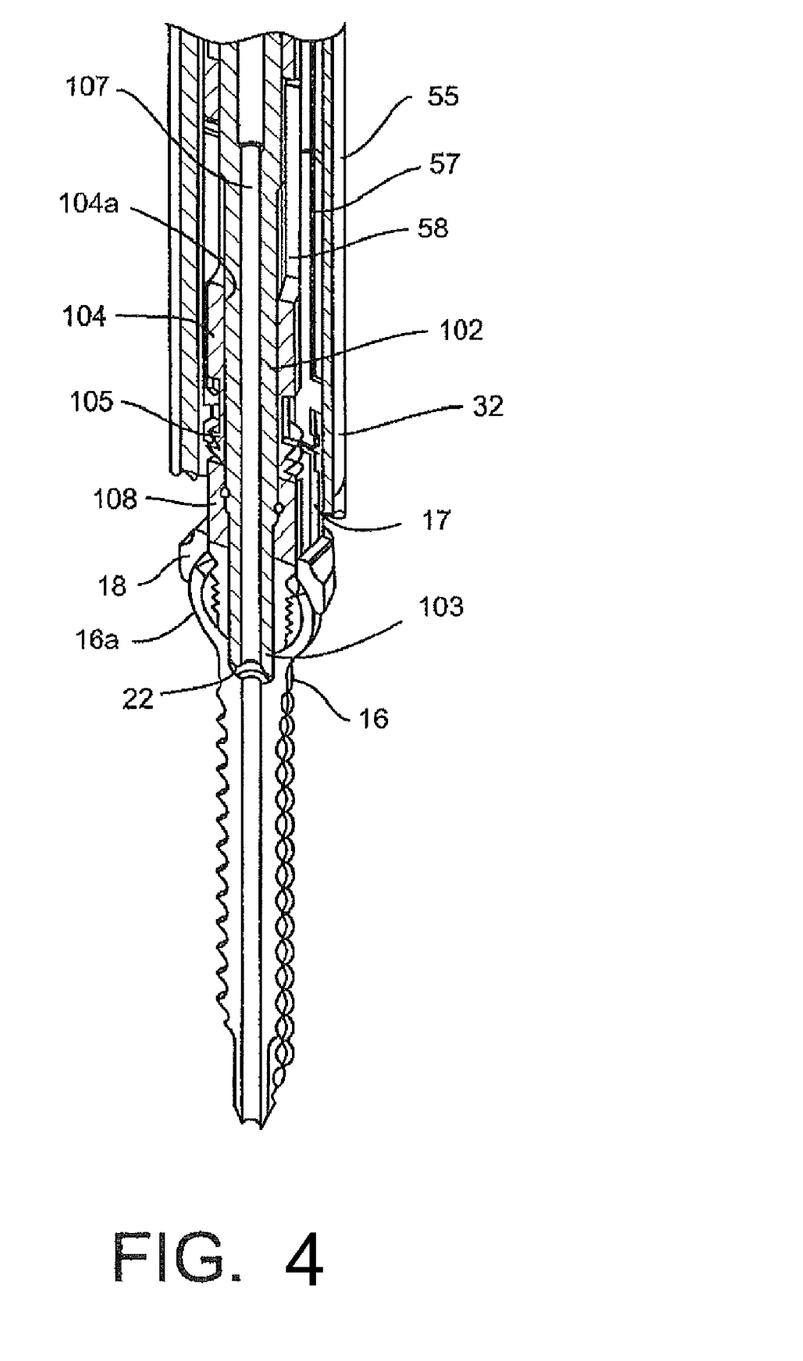
FIG. 4 is a cross-sectional view of the bone screw, screw extension assembly and screw driver shown in FIG. 3

By reference also to FIGS. 3-4, a screw driver 100 is shown in assembled engagement with the multi-axial bone screw 15. In this first procedure, the pedicle screw 15 with the attached screwdriver 100 is adapted for use particularly in the percutaneous procedures described in the co-pending, commonly assigned '979 Application referenced hereinabove. In the '979 Application screw extension assemblies 32 are described as being releasably attached to bone screws for use in percutaneous placement of spinal connecting rods between two or more pedicle screws to form a spinal fixation construct. In such procedure a single incision is described as being made for the insertion of each pedicle screw 15, the pedicle screw 15 with attached extension assembly 32 being inserted through each respective incision. A connecting rod is percutaneously connected to the pedicle screws through slots in the screw extension assemblies by a separate rod introducer as further described in the '979 Application. The screw extension assembly 32 includes an elongate hollow outer sleeve 55 within which an elongate hollow inner sleeve 57 is disposed. The screw extension assembly 32 is also configured to accept tools for access to the bone screw assembly and insertion of the bone screw. For instance, the bore 58 of the inner sleeve 57 of screw extension assembly 32 is sized to receive the screw driver 100 as shown in FIGS. 3-4. The screw driver 100 includes at the proximal end a handle 101 connected to a shaft 102 to permit manual rotation of the shaft. The shaft 102 includes at the distal end a tip defining an engagement end 103 that is configured to engage a drive tool recess 22 in the base of the bone screw head 16a. The engagement end and drive tool recess can be configured in a conventional manner, such as with a hex or Torx feature. The shaft 102 is sized so that the engagement end 103 can be received within the recess 22 while the handle 101 is accessible at the proximal end of the screw extension assembly 32. A coupling member 78 may be included on the screw extension assembly 32 for coupling to a rod persuader instrument (not shown).

The screw driver tool 100 includes an outer retention sleeve 104 having an interior bore 104a through which the shaft 102 extends. The shaft 102 and retention sleeve 104 are coupled to each other to allow free relative axial and rotational movement therebetween. The distal end 105 of the retention sleeve 104 is provided with exterior threads to match the internal threads on the interior surfaces of yoke 17. The retention sleeve 104 is connected to a knob 106 (FIG. 3) situated on or adjacent the proximal end of the screw extension assembly 32 that is configured to facilitate manual rotation of the retention sleeve to thread the distal end 105 into the yoke. A stop 108 is rotatably mounted on the shaft 102 and is configured to seat within the slot of the yoke 17 to support the shaft and retain the sleeve. Upon threaded connection of the outer retention sleeve 104 to the yoke 17, the retention sleeve 104 bears against the stop 108 and the stop bears against the yoke to provide joint rotational movement of the retention sleeve, stop and yoke. Prior to such threaded connection, the engagement end 103 of the inner shaft is guided into the drive tool recess 22 in the base of the bone screw head 16a. The stop 108 may be sized to prevent threading of the retention sleeve into the yoke unless and until the end 103 of the shaft is engaged within the tool recess of the bone screw. Once the tool 100 is properly seated, rotation of the handle 101 that is connected to the shaft 102 will rotate the bone screw shank 16. With the screw extension assembly 32 and the retention sleeve 104 attached to the yoke for joint movement, and with the yoke 17 being able to freely articulate with respect to screw shank 16, the screw extension assembly 32 may be manually held while the handle 101 is rotated to drive the screw shank 16 into a pedicle of a vertebra.

The screw extension assembly thus provides an avenue for guiding the screw driver instrument 100 into engagement with the bone screw. Even if the screw extension assembly is articulated relative to the bone screw, a minor manipulation of the assembly will automatically align the screw driver instrument with the drive tool recess. Once engaged the screw driver can be used to thread the bone screw 15 into the vertebra in a known manner and removed from the screw extension assembly. The shaft 102 of the screw driver 100 may be provided with a guide wire lumen 107 to allow introduction of the tool over a previously positioned guide wire.

Figure 5:
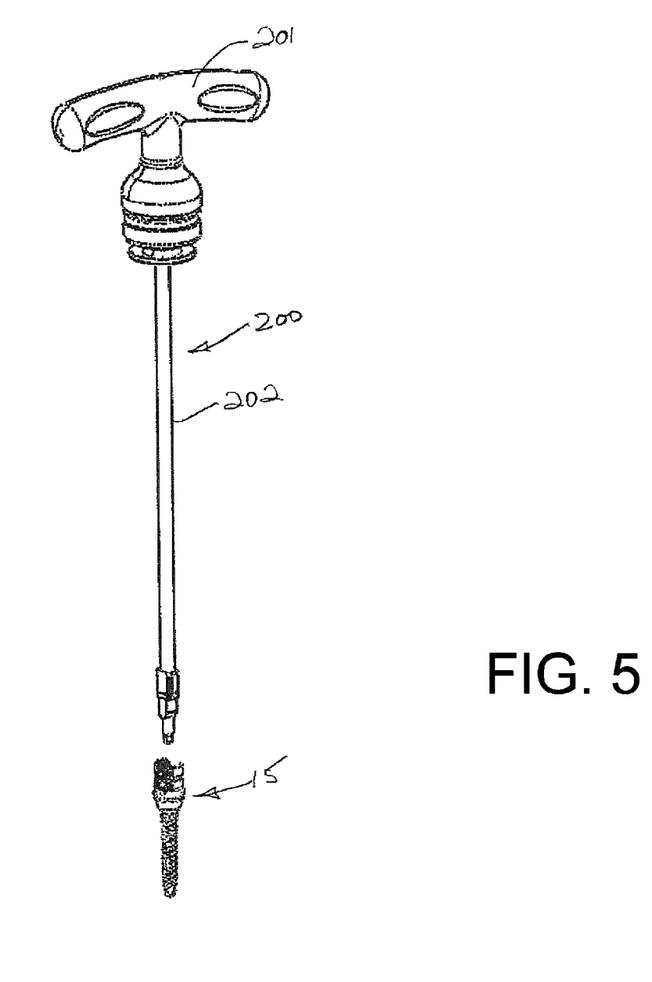
FIG. 5 is an exploded perspective view of the bone screw of FIG. 4 and a screw driver in accordance with another procedure disclosed herein.
Figure 6:
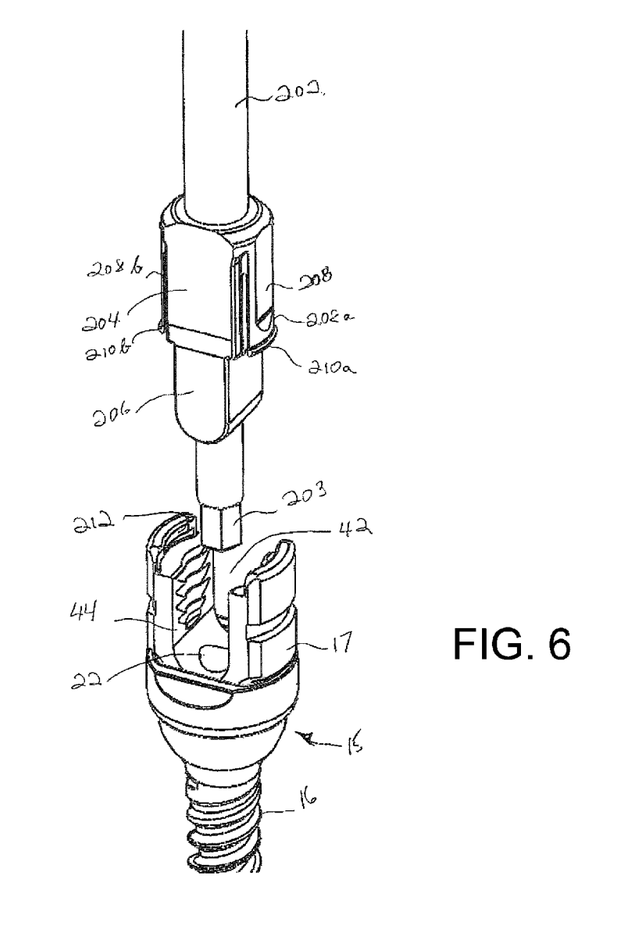
FIG. 6 is an enlarged exploded perspective view of the engagement portions of the bone screw and screw driver of FIG. 5.
Figure 7:
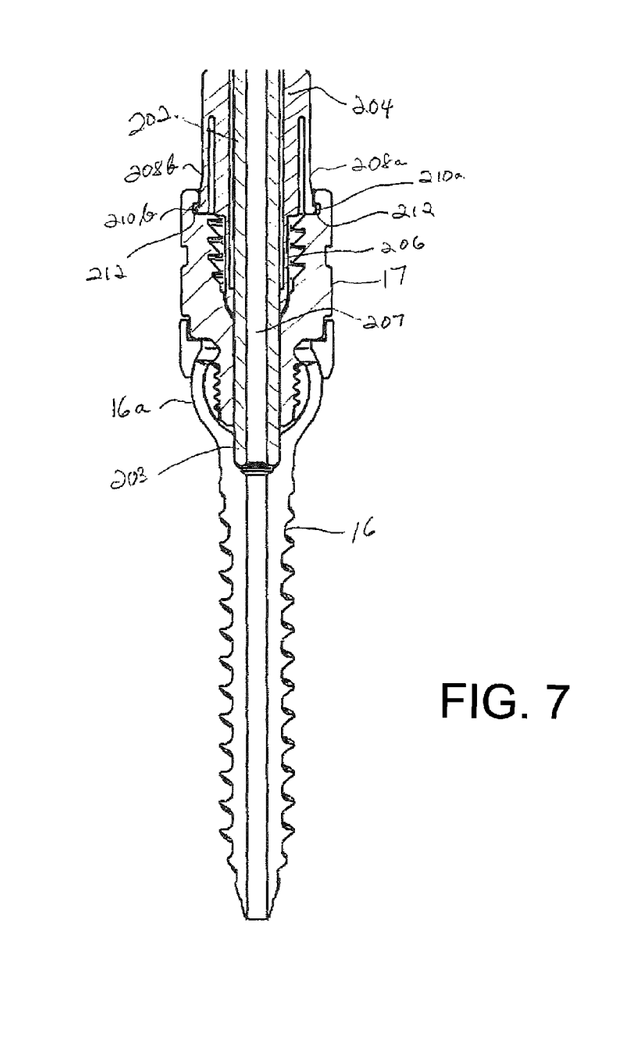
FIG. 7 is a cross-sectional view of the bone screw and screw driver of FIG. 5 with the screw driver engaged with the bone screw.

In another procedure, a screw driver may be used for insertion of a multi-axial bone screw in a spinal surgery known as a mini-open procedure. In the mini-open procedure a spinal fixation construct may be formed to connect to two or more pedicle screws with a spinal rod. A single incision may be formed over the pedicles by what is known in the art as a Wiltse-style approach and retracted sufficiently for the pedicle screws to be introduced through the incision on one side of the spine. Once the pedicle screws are placed, the spinal rod may also be introduced through the same single incision. As shown in FIGS. 5-7, a multi-axial bone screw, such as the bone screw 15 used in the percutaneous procedure described hereinabove, may be used together with a screwdriver 200 in the mini-open procedure. Unlike the percutaneous procedure, no screw extension assemblies are typically used in the mini-open procedure.

The screw driver 200 includes at the proximal end a handle 201 connected to a shaft 202 to permit manual rotation of the shaft. The shaft 202 includes at the distal end a tip defining an engagement end 203 that is configured to engage the drive tool recess 22 in the base of the bone screw head 16a. The engagement end and drive tool recess can be configured in a conventional manner similar to screw driver tip 103 to have a hex or Torx feature. The shaft 202 is sized and of length so that the engagement end 203 can be received within the recess 22 while handle 201 is accessible at the proximal end outside the patient. The shaft 202 of the screwdriver 200 may be cannulated by providing a guide wire lumen 207 through the shaft 202 to allow introduction of the tool over a previously positioned guide wire which would also be used to guide the introduction of the cannulated bone screw 15.

The screw driver 200 includes adjacent the distal end of the shaft 202 and spaced proximally from tip 203 an engagement member 204. Engagement member 204 is affixed to the shaft 202 for joint rotational movement therewith. Engagement member 204 includes at its distal end a stop 206 that is shaped and configured to seat within the slot 42 of the yoke 17. The stop 206 is configured to rotate the yoke 17 upon rotation of the shaft 202 as the engagement end 203 drives the threaded shank 16 into a pedicle of a vertebra.

The engagement member 204 includes a releasable retention member 208 for releasable attachment to the yoke 17. Releasable retention member 208 comprises a pair of flexible elements 208a and 208b. Flexible elements 208a and 208b are preferably cantilevered spring elements each having an outward projection 210a and 210b, respectively, at the free ends thereof. Flexible elements 208a and 208b are formed to provide an outward bias. The outward projections 210a and 210b are configured and shaped to releasably engage undercuts 212 extending into the interior surfaces 44 of each of the upstanding apposed arms of the yoke 17 with the flexible elements 208a and 208b providing an outward bias against the yoke arms. In addition to the releasable retention member 208 releasably retaining the screw driver 200 attached to the bone screw 15, the flexible elements 208a and 208b may provide an audible click upon attachment of the screw driver 200 to the bone screw 15 allowing the surgeon to known that proper attachment has been made.

Once engaged, the screw driver 200 can be used to thread the bone screw 15 into the vertebra in a known manner. With the engagement portion 204 affixed to the shaft 202, it can be seen that upon rotation of the shaft 202 by the handle 201, the screw 15 including its threaded shank 16 and yoke 17 will be jointly rotated upon rotation of the shaft 202. Upon completion of threaded insertion of the bone screw 15, the screw driver 200 may then be removed. A manual force applied by the surgeon to the handle in the proximal direction is sufficient to overcome the bias of the flexible elements 208a and 208b and separate the screw driver 200 from the screw 15.

Figure 8:
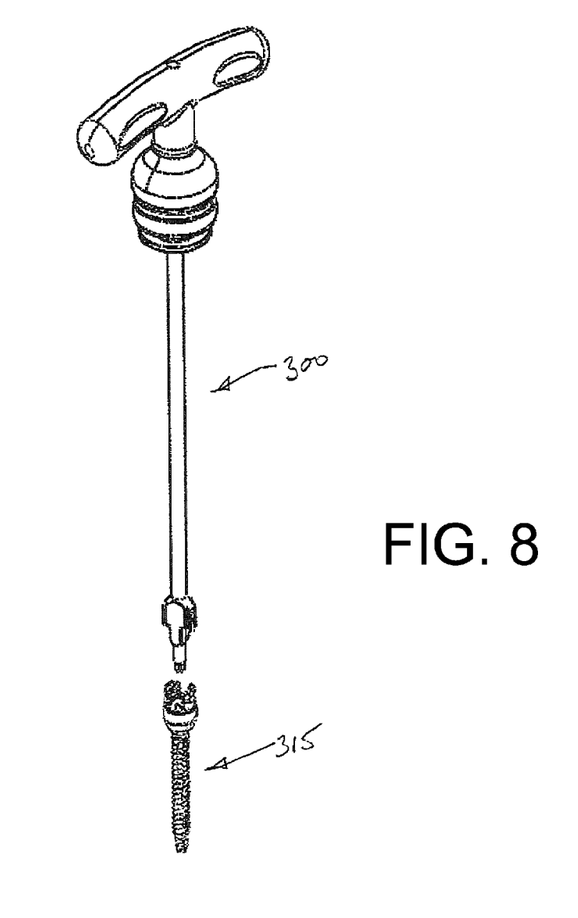
FIG. 8 is an exploded perspective view of a bone screw and a screw driver in accordance with a further procedure disclosed herein.
Figure 9:
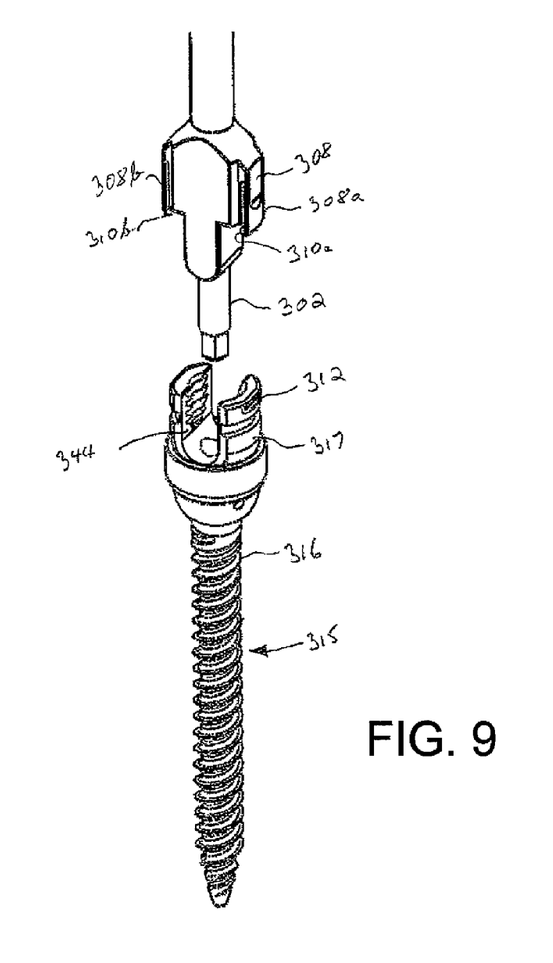
FIG. 9 is an enlarged exploded perspective view of the engagement portions of the bone screw and screw driver of FIG. 8.

In a further procedure, a screw driver may be used for insertion of a multi-axial bone screw in an open spinal procedure. In an open procedure a spinal fixation construct may be formed to connect to two or more pedicle screws with a spinal rod in single or multi-level surgeries. The incision may be formed midline through the patient's tissue with significant muscle retraction to permit introduction of the pedicle screws and the rod to form a construct on both sides of the spine through the one incision. As shown in FIGS. 8-9, a multi-axial bone screw 315 used may be used together with a screwdriver 300 in such an open procedure. Like the mini-open procedure, no screw extension assemblies are typically used in the open procedure.

In the open procedure the multi-axial bone 315 may be the screw described in the above-referenced co-pending, commonly assigned '898 Application. Such a screw 315 is substantially similar to bone screw 15 described herein except that the internal surfaces 344 of the upstanding opposed arms of yoke 317 are not provided with undercuts. Instead, the exterior surfaces of each arm of yoke 317 are respectively provided with an inwardly directed slot 312 located adjacent the upper end of each yoke arm as shown in FIG. 9. In addition, the threaded shank 316 of the bone screw 315 is not cannulated unlike shank 16 of screw 15. The construction of the screw driver 300 is substantially the same as the screw driver 200 except that the flexible elements 308a and 308b of releasable retention member 308 are formed to provide an inward bias with projections 310a and 310b extending releasably into the slots 312 in the exterior surfaces of the yoke arms. As such, flexible elements 308a and 308b attach releasably to the outside of the yoke 317 and may provide an audible click upon such attachment. Also, since the screw 315 is not cannulated there is no internal lumen provide through the shaft 302 of screw driver 300.

While the invention has been illustrated and described in detail in the drawings and foregoing description, the same should be considered as illustrative and not restrictive in character. For example, the screws 15 used in the mini-open procedure may, if desired, be used in an open procedure and as such, the screw drivers associated therewith may likewise be so used. It is understood that only the preferred embodiments have been presented and that all changes, modifications and further applications that come within the spirit of the invention are desired to be protected.

What is claimed is:

1. A screw driver for driving a multi-axial bone screw into a vertebra of a spine, the bone screw including an elongate shaft having a threaded screw portion at the distal end and a screw head at the proximal end, and a yoke articulatingly attached to the screw head, the yoke having a slot therethrough for receiving a connecting rod and including a lower surface, the yoke having an opening communicating with the screw head, said screw driver comprising:
   an elongate inner shaft having a distal end and a proximal end, said inner shaft defining a driving tip at said distal end configured to engage the screw head for rotation thereof;
   an outer retention sleeve disposed about said inner shaft and having a distal end and a proximal end, the inner shaft being freely rotatable within said outer retention sleeve and including said tip at the distal end thereof, the distal end of said outer retention sleeve configured to releasably engage the yoke for joint rotational movement therewith; and
   a stop rotatably mounted on said inner shaft between the distal end of the outer retention sleeve and the driving tip at the distal end of said inner shaft, said stop being sized to seat within the slot of said yoke and configured to rotate with rotation of said yoke;
   wherein rotation of said inner shaft rotates the elongate shaft of said bone screw relative to the said outer retention sleeve, said stop and said yoke which are joined in common.

2. A screw driver for driving a multi-axial bone screw into a vertebra of a spine, the bone screw including an elongate shaft having a threaded screw portion at the distal end and a screw head at the proximal end, and a yoke articulatingly attached to the screw head, the yoke having a slot therethrough for receiving a connecting rod and including a lower surface, the yoke having an opening communicating with the screw head, said screw driver comprising:
   an elongate shaft having a distal end and a proximal end, said shaft defining a driving tip at said distal end configured to engage the screw head for rotation thereof; and
   a screw engagement member affixed to said shaft for joint rotational movement therewith, said screw engagement member comprising a stop sized to seat within the slot of said yoke and configured to rotate said yoke upon rotation of said shaft, and a flexible retention member for releasable attachment to said yoke.

3. The screwdriver of claim 2, in which the slot of said yoke is defined by a pair of upstanding opposed arms having interior surfaces and exterior surfaces respectively and wherein said flexible retention member comprises a pair of flexible elements releasably attachable to said respective pair of arms.

4. The screwdriver of claim 3, wherein each of said opposed arms of said yoke comprises an undercut extending respectively into an interior surface thereof and wherein each of said flexible elements is configured to provide an outward bias and having a projection for flexibly and releasably extending into said respective interior undercuts in said arms.

5. The screwdriver of claim 3, wherein each of said opposed arms of said yoke comprises a slot extending respectively into an exterior surface thereof and wherein each of said flexible elements is configured to provide an inward bias and having a projection for flexibly and releasably extending into said respective exterior slots in said arms.

6. The screwdriver of claim 2, further including a handle fixed to said shaft at said distal end thereof, said shaft being of length such that said distal end with said handle extends outside a patient as said bone screw is driven into a vertebra of the spine.

7. The screwdriver of claim 2, further comprising a guide wire lumen extending through said shaft to allow introduction of the shaft over a previously positioned guide wire.

* * * * *